United States Patent
Assell et al.

[11] Patent Number: 6,022,376
[45] Date of Patent: *Feb. 8, 2000

[54] PERCUTANEOUS PROSTHETIC SPINAL DISC NUCLEUS AND METHOD OF MANUFACTURE

[75] Inventors: Robert L. Assell, Mendota Heights, Minn.; Charles D. Ray, Williamsburg, Va.

[73] Assignee: RayMedica, Inc., Bloomington, Minn.

[*] Notice: This patent is subject to a terminal disclaimer.

[21] Appl. No.: 09/039,582

[22] Filed: Mar. 16, 1998

Related U.S. Application Data

[63] Continuation-in-part of application No. 08/870,866, Jun. 6, 1997.

[51] Int. Cl.$^7$ .................................................... A61F 2/44
[52] U.S. Cl. .................................................................. 623/17
[58] Field of Search ........................... 623/8, 17; 606/61, 606/71

[56] References Cited

U.S. PATENT DOCUMENTS

| | | | |
|---|---|---|---|
| 3,875,595 | 4/1975 | Froning | 3/1 |
| 3,883,902 | 5/1975 | Lynch | 3/36 |
| 3,948,254 | 4/1976 | Zaffaroni | 128/127 |
| 4,349,921 | 9/1982 | Kuntz | 3/1 |
| 4,772,287 | 9/1988 | Ray et al. | 623/17 |
| 4,863,477 | 9/1989 | Monson | 623/17 |
| 4,904,260 | 2/1990 | Ray et al. | 623/17 |
| 4,911,718 | 3/1990 | Lee et al. | 623/17 |
| 4,932,969 | 6/1990 | Frey et al. | 623/17 |
| 4,932,975 | 6/1990 | Main et al. | 623/17 |
| 5,047,055 | 9/1991 | Bao et al. | 623/17 |
| 5,171,280 | 12/1992 | Baumgartner | 623/17 |
| 5,192,326 | 3/1993 | Bao et al. | 623/17 |
| 5,258,043 | 11/1993 | Stone | 623/66 |
| 5,306,308 | 4/1994 | Gross et al. | 623/17 |
| 5,306,309 | 4/1994 | Wagner et al. | 623/17 |
| 5,320,644 | 6/1994 | Baumgartner | 623/17 |
| 5,390,683 | 2/1995 | Pisharodi | 128/898 |
| 5,401,269 | 3/1995 | Büttner-Janz et al. | 623/17 |
| 5,443,514 | 8/1995 | Steffe | 623/17 |
| 5,458,642 | 10/1995 | Beer et al. | 623/17 |
| 5,458,643 | 10/1995 | Oka et al. | 623/18 |
| 5,514,180 | 5/1996 | Heggeness et al. | 623/17 |
| 5,534,028 | 7/1996 | Bao et al. | 623/17 |
| 5,534,030 | 7/1996 | Navarro et al. | 623/17 |
| 5,545,229 | 8/1996 | Parsons et al. | 623/17 |
| 5,562,738 | 10/1996 | Boyd et al. | 623/17 |
| 5,571,189 | 11/1996 | Kuslich | 623/17 |
| 5,645,597 | 7/1997 | Krapiva | 623/17 |
| 5,674,294 | 10/1997 | Bainville et al. | 623/17 |
| 5,674,295 | 10/1997 | Ray et al. | 623/17 |
| 5,674,296 | 10/1997 | Bryan et al. | 623/17 |
| 5,702,449 | 12/1997 | McKay | 623/17 |
| 5,702,450 | 12/1997 | Bisserie | 623/17 |
| 5,705,780 | 1/1998 | Bao | 204/157.15 |

FOREIGN PATENT DOCUMENTS

| | | |
|---|---|---|
| 2 639 823-A1 | 8/1990 | France . |
| 895433 | 1/1982 | Russian Federation . |
| WO 94/23671 | 10/1994 | WIPO . |

OTHER PUBLICATIONS

Article entitled, The Artificial Disc Introduction, History and Socioeconomics, by Charles Dean Ray; pp. 205–225; dated 1992.

*Primary Examiner*—Michael J. Milano
*Attorney, Agent, or Firm*—Dicke, Billig & Czaja, P.A.

[57] ABSTRACT

A capsule-shaped prosthetic spinal disc nucleus for implantation into a human intradiscal space, made of a substantially inelastic constraining jacket surrounding an amorphous polymer core. The constraining jacket has a generally fixed maximum volume and defines a height. The amorphous polymer core fills an initial volume of the constraining jacket and develops an internal pressure. In response to the internal pressure, the constraining jacket transitions toward the maximum volume, increasing substantially in height.

26 Claims, 8 Drawing Sheets

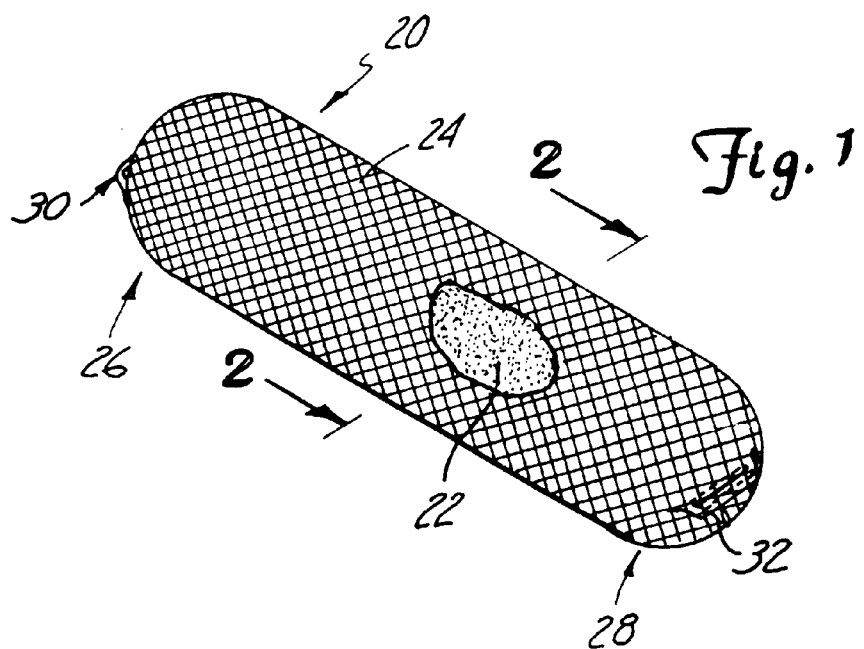
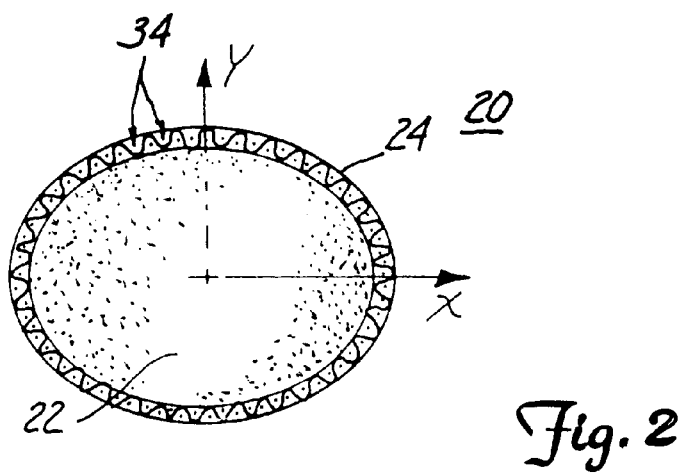

PERCUTANEOUS PROSTHETIC SPINAL DISC NUCLEUS AND METHOD OF MANUFACTURE

CROSS-REFERENCE TO CO-PENDING APPLICATION

This is a continuation-in-part of co-pending application Ser. No. 08/870,866 filed on Jun. 6, 1997.

BACKGROUND OF THE INVENTION

The present invention relates to a prosthetic spinal disc nucleus. More particularly, it relates to a percutaneously implantable, capsule-shaped intradiscal prosthesis and a method of manufacture therefor.

The vertebral spine is the axis of the skeleton upon which all of the body parts "hang". In humans, the normal spine has seven cervical, twelve thoracic and five lumbar segments. The lumbar segments sit upon the sacrum, which then attaches to the pelvis, in turn supported by the hip and leg bones. The bony vertebral bodies of the spine are separated by intervertebral discs, which act as joints, but allow known degrees of flexion, extension, lateral bending and axial rotation.

The typical vertebra has a thick interior bone mass called the vertebral body, with a neural (vertebral) arch that arises from a posterior surface of the vertebral body. Each narrow arch combines with the posterior surface of the vertebral body and encloses a vertebral foramen. The vertebral foramina of adjacent vertebrae arc aligned to form a vertebral canal, through which the spinal sac, cord and nerve rootlets pass. The portion of the neural arch that extends posteriorly and acts to protect a posterior side of the spinal cord is known as the lamina. Projecting from the posterior region of the neural arch is a spinous process. The centra of adjacent vertebrae are supported by the intervertebral disc.

The intervertebral disc primarily serves as a mechanical cushion between the vertebral bones, permitting controlled motions within vertebral segments of the axial skeleton. The normal disc is a unique, mixed structure, comprised of three component tissues: The nucleus pulposus ("nucleus"), the anulus fibrosus ("anulus"), and two opposing vertebral end plates. The two vertebral end plates are each composed of thin cartilage overlying a thin layer of hard, cortical bone which attaches to the spongy, richly vascular, cancellous bone of the vertebral body. The end plates thus serve to attach adjacent vertebrae to the disc. In other words, a transitional zone is created by the end plates between the malleable disc and the bony vertebrae.

The anulus of the disc is a tough, outer fibrous ring that binds together adjacent vertebrae. This fibrous portion, which is much like a laminated automobile tire, is generally about 10 to 15 millimeters in height and about 15 to 20 millimeters in thickness. The fibers of the anulus consist of 15 to 20 overlapping multiple plies, and are inserted into the superior and inferior vertebral bodies at roughly a 30° angle in both directions. This configuration particularly resists torsion, as about half of the angulated fibers will tighten when the vertebrae rotate in either direction, relative to each other. The laminated plies are less firmly attached to each other.

Immersed within the anulus, positioned much like the liquid core of a golf ball, is the nucleus. The healthy nucleus is largely a gel-like substance having a high water content, and similar to air in a tire, serves to keep the anulus tight yet flexible. The nucleus-gel moves slightly within the anulus when force is exerted on the adjacent vertebrae with bending, lifting, etc.

The nucleus and the inner portion of the anulus have no direct blood supply. In fact, the principal nutritional source for the central disc arises from circulation within the vertebral body. Microscopic, villous-like fingerlings of the nuclear and anular tissue penetrate the vertebral end plates and allow fluids to pass from the blood across the cell membrane of the fingerlings and then inward to the nuclear tissue. These fluids are primarily body water and the smallest molecular weight nutrients and electrolytes.

The natural physiology of the nucleus promotes these fluids being brought into and released from the nucleus by cyclic loading. When fluid is forced out of the nucleus, it passes again through the end plates and then back into the richly vascular vertebral bodies. The cyclic loading amounts to daily variations in applied pressure on the vertebral column (e.g., body weight and muscle pull) causing the nucleus to expel fluids, followed by periods of relaxation and rest, resulting in fluid absorption or swelling by the nucleus. Thus, the nucleus changes volume under loaded and non-loaded conditions. Further, the resulting tightening and loosening effect on the anulus stimulates normal anulus collagen fibers to remain healthy or to regenerate when torn, a process found in all normal ligaments related to body joints. Notably, the ability of the nucleus to release and imbibe fluids allows the spine to alter its height and flexibility through periods of loading or relaxation. Normal loading cycling is thus an effective nucleus and inner anulus tissue fluid pump, not only bringing in fresh nutrients, but perhaps more importantly, removing the accumulated, potentially autotoxic by-products of metabolism.

The spinal disc may be displaced or damaged due to trauma or a disease process. A disc herniation occurs when the anulus fibers are weakened or torn and the inner tissue of the nucleus becomes permanently bulged, distended, or extruded out of its normal, internal anular confines. The mass of a herniated or "slipped" nucleus can compress a spinal nerve, resulting in leg pain, loss of muscle control, or even paralysis. Alternatively, with discal degeneration, the nucleus loses its water binding ability and deflates, as though the air had been let out of a tire. Subsequently, the height of the nucleus decreases, causing the anulus to buckle in areas where the laminated plies are loosely bonded. As these overlapping laminated plies of the anulus begin to buckle and separate, either circumferential or radial anular tears may occur, which may contribute to persistent and disabling back pain. Adjacent, ancillary spinal facet joints will also be forced into an overriding position, which may create additional back pain.

Whenever the nucleus tissue is herniated or removed by surgery, the disc space will narrow and may lose much of its normal stability. In many cases, to alleviate pain from degenerated or herniated discs, the nucleus is removed and the two adjacent vertebrae surgically fused together. While this treatment alleviates the pain, all discal motion is lost in the fused segment. Ultimately, this procedure places greater stresses on the discs adjacent to the fused segment as they compensate for the lack of motion, perhaps leading to premature degeneration of those adjacent discs. A more desirable solution entails replacing in part or as a whole the damaged nucleus with a suitable prosthesis having the ability to complement the normal height and motion of the disc while stimulating the natural disc physiology.

Restoring the nutrition-flushing cycle of a natural disc is important for a prosthetic spinal disc nucleus to be successful. Vascular circulation and nerve supply to the disc is limited to the outer layers of the anulus, never penetrating more than a few millimeters, or about five of the anular plies. Most of the nutrition for the inner anulus and nucleus is provided by diffusion through the end plates of the vertebral bodies and by the important pumping action between the partially loaded and fully loaded conditions of the disc. If the nutritional cycle is impeded, a variety of degenerative changes may occur. Nutrition to the inner disc slowly ceases, resulting in intradiscal build-up of acids and autotoxins, and other changes. This is followed by nuclear and anular fiber degeneration, shrinkage of the nucleus, segmental laxity, spur formation, disc space collapse and perhaps spontaneous fusion. Additionally, significantly disabling back pain may develop.

As an alternative to vertebral fusion, various prosthetic discs have been developed. The first prostheses embodied a wide variety of ideas, such as ball bearings, springs, metal spikes and other perceived aids. These prosthetic discs were designed to replace the entire intervertebral disc space and were large and rigid. Beyond the questionable applicability of these devices is the inherent difficulties encountered during implantation. Due to their size and inflexibility, these devices required an anterior implantation approach as the barriers presented by the lamina and, more importantly, the spinal cord and nerve rootlets during posterior implantation could not be avoided. Recently, smaller and more flexible prosthetic nucleus devices have been developed. With the reduction in prosthesis size, the ability to work around the spinal cord and nerve rootlets during posterior implantation has become possible.

One such application utilizes a hydrogel-based material as a replacement for the natural nucleus. For example, Bao et al., U.S. Pat. No. 5,047,055, discloses a prosthetic nucleus for a vertebral disc made of a hydrogel material. Prior to implant, the hydrogel material is implanted into the intradiscal space in a dehydrated state. The hydrogel material then hydrates to a shape conforming to the natural nucleus. Similarly, Bao et al., U.S. Pat. No. 5,192,326, describes a prosthetic nucleus comprised of a solid hydrogel core or a multiplicity of hydrogel beads surrounded by a membrane. Once again, this prosthesis is implanted into the disc space in a dehydrated state, subsequently hydrating to a shape conforming to the natural nucleus.

While posterior implantation is available with the devices described in the two Bao patents, several drawbacks exist. For example, because the prosthesis is purposefully designed to match the shape of the nucleus cavity, accurate orientation of the prosthetic disc within the nucleus cavity prior to hydration is difficult to ascertain. Additionally, the Bao devices rely solely upon the natural anulus to constrain expansion of the hydrogel core. Obviously, with most applications, the anulus is already damaged, and any additional forces placed upon the anulus by the prosthesis may impede healing and even cause further deterioration. Similarly, implantation of the Bao devices inherently requires imparting an opening through the anulus. Because the Bao devices rely exclusively on the anulus for expansion constraint, there is a distinct possibility that the prosthesis may migrate out from the nucleus cavity through the hole in the anulus. Further, the hydrogel bead-based prosthesis requires molding hydrogel beads to a size of 40–120 $\mu$m. Beyond the costs associated with creating an appropriately sized mold, the spherical-shaped beads inherently result in undesirable spacing between individual beads. In other words, upon hydration, the hydrogel beads are not compactly stacked, resulting in a prosthesis that may not provide necessary intradiscal support.

Degenerated, painfully disabling interspinal discs are a major economic and social problem for patients, their families, employers and the public at large. Any significant means to correct these conditions without further destruction or fusion of the disc may therefore serve an important role. Other means to replace the function of a degenerated disc have major problems such as complex surgical procedures, unproven efficacy, place unnecessary and possibly destructive forces on an already damaged anulus, etc. Therefore, a substantial need exists for an easily-implantable prosthetic spinal disc nucleus that restores the size, load-bearing ability and pumping action of a normal disc while minimizing any additional trauma to the disc space.

SUMMARY OF THE INVENTION

The present invention provides an elongated prosthetic spinal disc nucleus for implantation deep inside a nucleus cavity of a human disc space and a method of manufacturing such a prosthesis. The nucleus cavity is defined by an opposing pair of vertebral bodies, forming opposing endplates, and an anulus. The prosthesis is comprised of a substantially inelastic constraining jacket maintaining an amorphous polymer core.

The constraining jacket is preferably flexible but inelastic, having a generally fixed maximum volume that is less than a volume of the nucleus cavity. The maximum volume of the constraining jacket is determined by a generally fixed circumference and length. Further, the constraining jacket defines a height corresponding to a plane substantially perpendicular to the opposing endplates.

The amorphous polymer core is flowable in at least a first state. The amorphous polymer core is disposed within the constraining jacket and is configured such that upon insertion, the amorphous polymer core fills an initial volume of the constraining jacket and creates an internal pressure within the constraining jacket. The constraining jacket, in turn, is configured to transition from the initial volume toward the maximum volume, increasing substantially in height in response to the internal pressure.

In one preferred embodiment, the amorphous polymer core is a hydrogel configured to expand from an unhydrated state to a hydrated state. With this embodiment, the maximum volume of the constraining jacket is greater than a volume of the hydrogel in the unhydrated state, but less than a theoretical, unconstrained volume of the hydrogel in the hydrated state. The internal pressure within the constraining jacket is a swelling pressure of the hydrogel transitioning from the unhydrated state to the hydrated state.

The preferred method of manufacturing a prosthetic spinal disc nucleus in accordance with the present invention includes providing a substantially inelastic constraining jacket and an amorphous polymer core that is flowable in at least a first state. The constraining jacket has a generally fixed maximum volume determined by a fixed circumference and length and defines a height corresponding to a transverse plane of the nucleus cavity. The maximum volume of the constraining jacket is less than a volume of the nucleus cavity.

The amorphous polymer core, in a flowable state, is inserted into the constraining jacket and fills an initial volume of the constraining jacket. An internal pressure is generated within the constraining jacket. The constraining jacket transitions from the initial volume toward the maximum volume and increases substantially in height in response to the internal pressure.

One preferred application includes implanting a properly sized constraining jacket into a nucleus cavity of a damaged disc space. The amorphous polymer core, in a flowable state, is then inserted into the constraining jacket, via a syringe or small diameter catheter. This insertion preferably occurs percutaneously. In an alternative embodiment, the amorphous polymer core is placed within the constraining jacket prior to implant.

Following implant, the prosthetic spinal disc nucleus of the present invention reestablishes near-normal disc height and near-normal anulus position and function. Additionally, by utilizing an amorphous polymer core, the prosthetic spinal disc nucleus is compliant such that the prosthesis will conform to the available internal shape of the nucleus cavity, although it does not encompass the entire cavity. Finally, the constraining jacket serves to direct and constrain the amorphous polymer core, minimizing transverse forces on an interior of the anulus.

BRIEF DESCRIPTION OF THE DRAWINGS

FIG. 1 is a perspective view of a prosthetic spinal disc nucleus, including a cut-away view showing a portion of a core, in accordance with the present invention;

FIG. 2 is a front sectional view of the prosthetic spinal disc nucleus along the line 2—2 of FIG. 1;

DETAILED DESCRIPTION OF THE INVENTION

Figure 3:
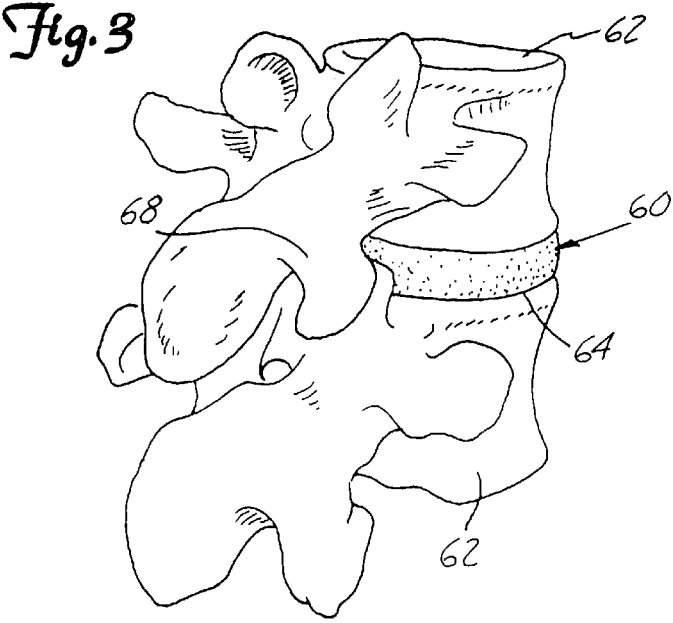
FIG. 3 is a posterior view of a spinal segment including a degenerated discal area.

A preferred embodiment of a prosthetic spinal disc nucleus 20 is shown in FIG. 1. The prosthetic spinal disc nucleus 20 is a capsule-shaped body comprised of an amorphous polymer core 22 and a constraining jacket 24. The constraining jacket 24 is defined by an anterior end 26 and a posterior end 28, and is secured around the amorphous polymer core 22 by an anterior closure 30 located at the anterior end 26 and a posterior closure 32 located at the posterior end 28.

Various components of the prosthetic spinal disc nucleus 20 are described in greater detail below. Generally speaking, however, the amorphous polymer core 22 is preferably configured to be flowable in at least a first state. The amorphous polymer core 22 is inserted into the constraining jacket 24, generating an internal pressure. The constraining jacket 24 is configured to be flexible, but substantially inelastic such that the prosthetic spinal disc nucleus 20 increases in a desired direction in response to the internal pressure.

A. Amorphous Polymer Core 22 As A Hydrogel

In a preferred embodiment, the amorphous polymer core 22 is a hydrogel configured to imbibe fluids, expanding from an unhydrated state to a hydrated state. In this regard, the hydrogel material is preferably formulated as a mixture of hydrogel polyacrylonitrile. In particular, acrylamide and acrylonitrile (block co-polymer) are used. Alternatively, the hydrogel material used for the amorphous polymer core 22 can be any hydrophilic acrylate derivative with a unique multiblock copolymer structure or any other hydrogel material having the ability to deform and reform in a desired fashion in response to placement and removal of loads. Even further, a biologically-safe polymer or elastomer that can imbibe fluids while maintaining its structure under various stresses is acceptable. For example, the amorphous polymer core 22 can be formulated as a mixture of polyvinyl alcohol and water. In one preferred embodiment, the hydrogel material used for the amorphous polymer core 22 is manufactured under the trade name HYPAN® by Hymedix International, Inc. of Dayton, N.J.

In one preferred embodiment, the hydrogel material of the amorphous polymer core 22 is in a powder form. In other words, the amorphous polymer core 22 preferably consists of a plurality of fine, irregularly shaped grains of hydrogel material. The grains are non-spherical. With this configuration, each of the grains of hydrogel material has a width on the order of $8 \times 10^{-3}$ inch. Acceptable powder hydrogel material is available, for example, under the tradename HYPAN® from Hymedix International, Inc. of Dayton, N.J. The hydrogel powder may be used as supplied by the manufacturer, or may be processed to generally orientate the shape of the individual grains. In a preferred embodiment, the individual grains have a flat side, and are defined by a height less than a length and a width. For example, each of the flattened hydrogel powder grains will preferably have a height, length and width aspect ratio of approximately 1:5:5. With this configuration, the flattened hydrogel powder grains will lie against one another when compacted, and have a tendency to slide. The shape of individual grains of the amorphous polymer core 22 may be further controlled, as described in greater detail below.

While each grain of hydrogel material of the amorphous polymer core 22 does have a discernable shape, the overall amorphous polymer core 22 does not. Therefore, the amorphous polymer core 22 has a fluid-like attribute such that in at least one state the amorphous polymer core 22 will flow. For example, in the preferred embodiment wherein the amorphous polymer core 22 is a powdered hydrogel, the individual grains are relatively small such that the powder as a whole "flows". This flowable attribute can be enhanced by coating the individual grains with a low friction material, such as polyvinyl alcohol or polyacrylonitrite.

While the amorphous polymer core 22 has been preferably described as consisting of a dry, hydrogel powder, other forms are acceptable. For example, the amorphous polymer core 22 may consist of a hydrogel powder, as described above, suspended in a viscous liquid. In one preferred embodiment, the viscous liquid is glycerine, although other similar fluid carriers able to suspend hydrogel powder can be used. Even further, the amorphous polymer core 22 may be a fluid hydrogel, consisting of dry hydrogel powder, as described above, dissolved in a solvent, such as Dimethyl Sulfoxide (DMSO). Other solvents able to keep the hydrogel polymer chains mobile are also available. The resulting fluid hydrogel is non-thixotropic. Prior to exposure to water (such as in a disc space), the fluid hydrogel flows. However, upon contact with water, the solvent is replaced by water, causing the fluid hydrogel to permanently congeal or solidify. Thus, upon hydration, the fluid hydrogel will fuse into solid form. It should be understood that the solid form of the fluid hydrogel will still have a conformability characteristic, such that the amorphous polymer core 22 will deform slightly in response to various loads.

Regardless of exact form, where a hydrogel material is used, the amorphous polymer core 22 expands from a dehydrated state (prior to implant) to a hydrated state (following implant). In the dehydrated state, the amorphous polymer core 22 flows, such that it can be poured or injected into the constraining jacket 24, as described below.

B. Constraining Jacket 24

Completely surrounding the amorphous polymer core 22 is the constraining jacket 24. The constraining jacket 24 is preferably a capsule-shaped tube made of a tightly-woven, high molecular weight, high tenacity polymeric fabric. In a preferred embodiment, high molecular weight polyethylene is used as the weave material for the constraining jacket 24. However, polyester or any other high molecular weight, high tenacity polymeric material can be employed, and carbon fiber yarns, ceramic fibers, metallic fibers, etc., are also acceptable. While the constraining jacket 24 is itself flexible, the material comprising the constraining jacket 24 is not. In other words, the material making up the constraining jacket 24 has virtually no stretch.

The constraining jacket 24 is preferably made of fibers that have been highly orientated along their length. As a result, the constraining jacket 24 material, while flexible, has little elasticity or stretch and a generally fixed maximum volume. The maximum volume of the constraining jacket 24 is defined by a generally fixed length and circumference. Additionally, with reference to FIG. 2, the constraining jacket 24 defines a height and a width. The height of the constraining jacket 24 corresponds to a transverse plane of a nucleus cavity (not shown) and is represented by the "x" plane in FIG. 2. Conversely, the width of the constraining jacket 24 corresponds to the sagittal plane of the nucleus cavity and is represented by the "y" plane in FIG. 2.

The preferred woven construction of the constraining jacket 24 creates a plurality of small openings 34, as shown in FIG. 2. The plurality of small openings 34 are large enough to allow bodily fluids to interact with the amorphous polymer core 22 otherwise maintained within the constraining jacket 24. However, the plurality of small openings 34 are small enough to prevent the individual particles of the amorphous polymer core 22 from escaping. Preferably, the plurality of small openings 34 have an average diameter smaller than the particle size of the individual grains of the amorphous polymer core 22, or about $8 \times 10^{-3}$ inches, although other dimensions are acceptable. While the constraining jacket 24 is described as having a weave configuration, any other configuration having a semi-permeable or porous attribute can be used, such as a self-sealing membrane.

The preferred woven construction of the constraining jacket 24 also provides a textured outer surface for purchase within the disc space, as described in greater detail below. Thus, the constraining jacket 24 prevents the prosthetic spinal disc nucleus 20 from spontaneously dislodging from the disc space. Additionally, the constraining jacket 24 material preferably allows for tissue ingrowth.

C. Construction of Prosthetic Spinal Disc Nucleus 20 With Hydrogel Material

In one embodiment, the prosthetic spinal disc nucleus 20 of the present invention is constructed by selecting the constraining jacket 24 sized to fit within a disc space (described below). The posterior end 28 of the constraining jacket 24 is sewn closed by the posterior closure 32, which is a stitching comprised of the same high-tenacity polymeric material, such as high molecular weight polyethylene, as is used for the constraining jacket 24. The amorphous polymer core 22 (in an unhydrated state) is poured into the constraining jacket 24 at the open, anterior end 26. The anterior end 26 is then closed by the anterior closure 30. Following closure of the anterior end 26 of the constraining jacket 24, the prosthetic spinal disc nucleus 20 is massaged to horizontally orientate the amorphous polymer core 22, partially flattening and narrowing the prosthetic spinal disc nucleus 20 in preparation for implantation.

As an alternative to pouring the amorphous polymer core 22 (in an unhydrated state) into the constraining jacket 24, the amorphous polymer core 22, due to a flowable attribute in at least a first state, may instead be injected within the constraining jacket 24 by a syringe or small diameter catheter. This approach is described in more detail below. Generally speaking, however, the constraining jacket 24 is scaled at both the anterior end 26 and posterior end 28. A syringe or small diameter catheter is passed through an outer wall of the constraining jacket 24 and an appropriate volume of the amorphous polymer core 22 is injected. To facilitate injection, the constraining jacket 24 may include a self-sealing mechanism. The self-sealing mechanism may assume a variety of forms, including a normally closed tube extending from the constraining jacket 24 that expands or opens with applied pressure (such as when the amorphous polymer core 22 is forced therethrough). Alternatively, the self-sealing mechanism may be a spiral tube that is normally closed until pressure is applied.

Regardless of whether the amorphous polymer core 22 is placed into the constraining jacket 24 before or after implant, an important concern is the actual amount or total volume of the amorphous polymer core 22 relative to the volume of the constraining jacket 24. The constraining jacket 24 has a generally fixed maximum volume. In a preferred embodiment, the volume of the amorphous polymer core 22 in an unhydrated state fills approximately 60%–80% of the available internal volume of the constraining jacket 24. Alternatively, the percent volumetric filling can be altered, either slightly higher or lower. As described in greater detail below, the volume of the amorphous polymer core 22, where a hydrogel material is used, will expand greatly upon hydration. Thus, while the volume of amorphous polymer core 22 in the dehydrated state is less than the internal volume of the constraining jacket 24, the theoretical volume of the amorphous polymer core 22 in an unconstrained, hydrated state is greater than the internal volume of the constraining jacket 24.

In addition to varying the volume of the amorphous polymer core 22 placed within the constraining jacket 24, other adjustments can be made to better meet the needs of a particular disc space. For example, the hydrogel material used for the amorphous polymer core 22 can be selected to have a higher or lower swelling behavior. Alternatively, the grains comprising the amorphous polymer core 22 can be coated with a hygroscopic film to increase overall flow by lowering the coefficient of friction between individual grains.

As described above, the generally fixed maximum volume of the constraining jacket 24 is greater than a volume of the hydrogel material used for the amorphous polymer core 22 in an unhydrated state. Conversely, the generally fixed maximum volume of the constraining jacket 24 is less than the volume of the amorphous polymer core 22 if allowed to hydrate fully without constraint. Thus, because the amorphous polymer core 22 has a natural hydrated volume greater than that of the constraining jacket 24, the constraining jacket 24 will be tight about the amorphous polymer core 22 when hydrated, as described in greater detail below. In this manner, the volume differential between the constraining jacket 24 and the amorphous polymer core 22 in a hydrated state serves to extend the useful life of the prosthetic spinal disc nucleus 20. In particular, the constraining jacket 24 effectively prevents the amorphous polymer core 22 from reaching a natural hydration level. Consequently, the amorphous polymer core 22 will have a constant affinity for imbibing additional fluid.

In final form, the prosthetic spinal disc nucleus 20 is preferably sized to conform to the approximate length of a sagittal diameter and an approximate height of an adult human disc nucleus cavity. For example, in one preferred embodiment, the prosthetic spinal disc nucleus 20 will have, in final form, a length in the range of approximately 10 to 35 millimeters and an outer diameter in the range of approximately 3 to 15 millimeters. The preferred prosthetic spinal disc nucleus 20 is 25 millimeters in length and 10 millimeters in outer diameter. It is realized that not all human disc nucleus cavities are of the same size. Therefore, the prosthetic spinal disc nucleus 20 can be constructed to assume a wide variety of dimensions. The appropriate size of the prosthetic spinal disc nucleus 20 for a particular patient is determined by various diagnostic procedures prior to and during surgery. Basically, the properly dimensioned prosthesis is a function of the patient's size and spinal level. By providing a different prosthetic spinal disc nucleus 20 with varying dimensions, the space requirements reflected by any spinal segment, human or animal, are satisfied.

Figure 4:
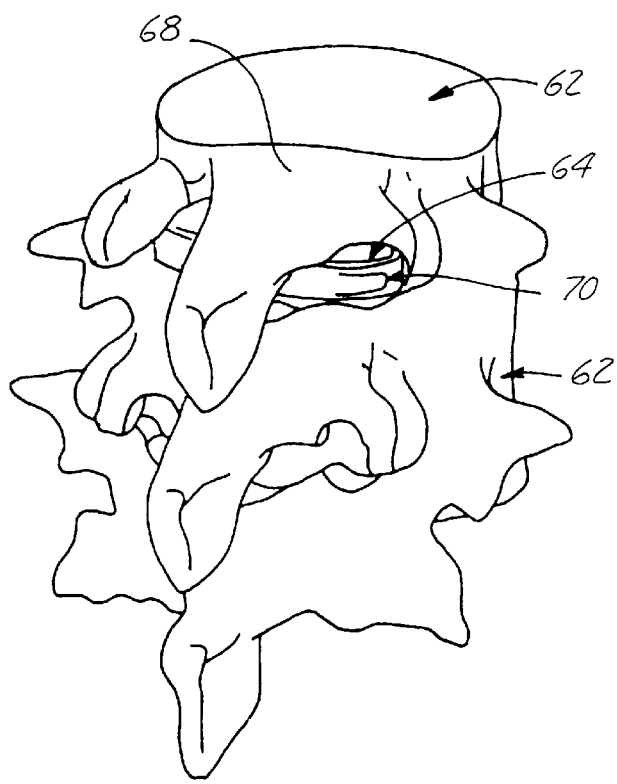
FIG. 4 is a posterior view of the spinal segment of FIG. 3 showing a flap that has been cut through an anulus.
Figure 5:
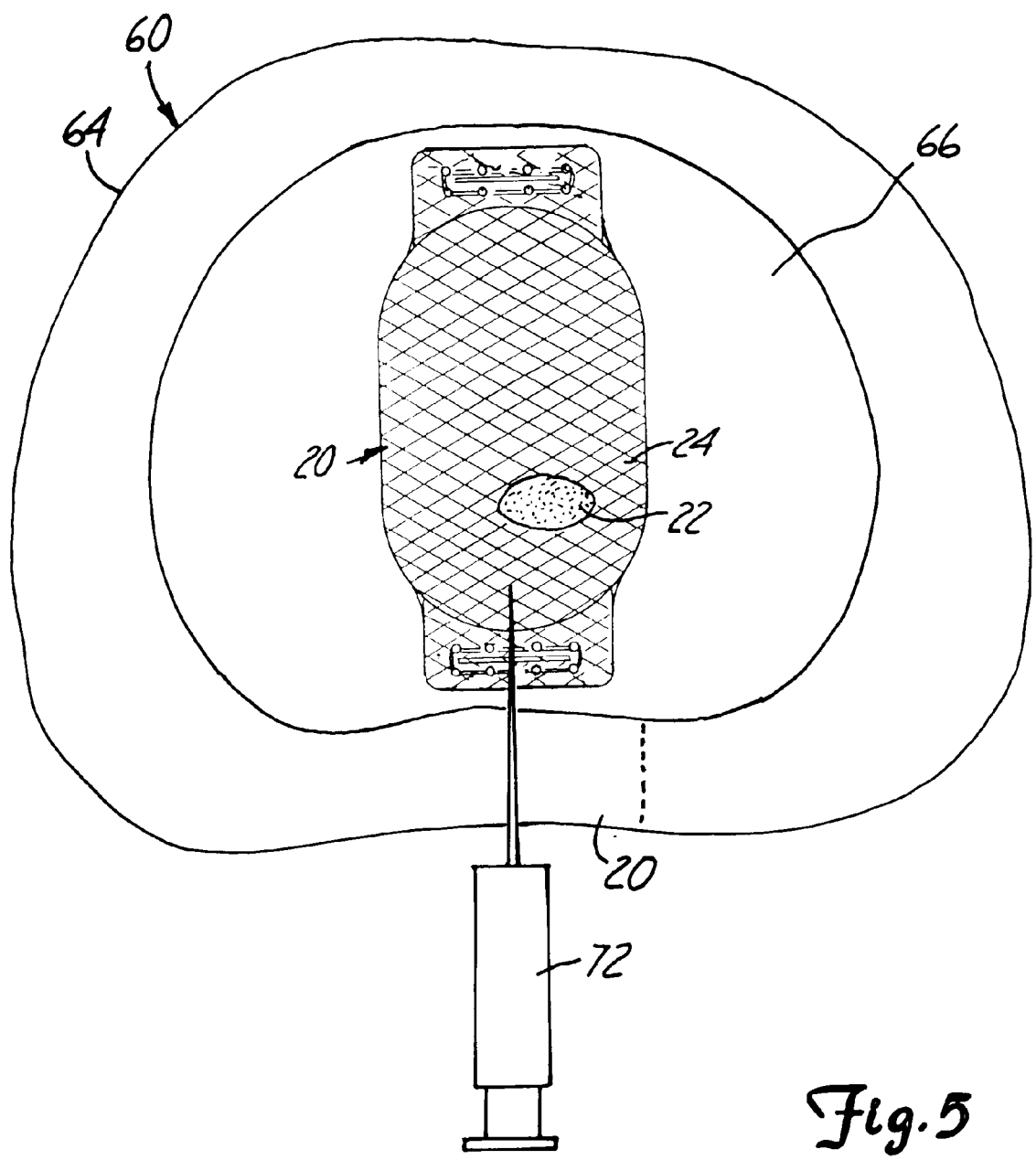
FIG. 5 is a top, sectional view of a human disc space having a prosthetic spinal disc nucleus in accordance with the present invention implanted.

D. Implantation and Function of The Prosthetic Spinal Disc Nucleus 20 With Hydrogel Material In one preferred embodiment, the prosthetic spinal disc nucleus 20 is preferably percutaneously implanted into a damaged disc space 60, shown in FIGS. 3–5. The disc space 60 separates two adjacent vertebrae 62, defining opposing endplates (not shown), and includes an anulus 64 and a nucleus cavity 66 (FIG. 5). Implantation is preferably performed via a posterior approach, although it should be understood that an anterior or oblique technique may also be employed. With the posterior method, a unilateral laminotomy in a targeted lamina area 68 may be required. As shown in FIG. 4, a flap 70 is created in the anulus 64, and, if necessary, excess material is removed from the nucleus cavity 66 (FIG. 5) to create room for the prosthetic spinal disc nucleus 20. The appropriate volume of the nucleus cavity 66 is estimated and the prosthetic spinal disc nucleus 20 is selected.

More particularly, the surgeon evaluates the disc space 60 in terms of pressure, volume, degree of disc distention or other visual clues. With this information in mind, an appropriately sized constraining jacket 24 (FIG. 1) is selected and placed through the flap 70. Notably, the opening provided by the flap 70 can be very small because the constraining jacket 24 is "empty" (i.e., does not initially contain the amorphous polymer core 22) and can therefore be compact for insertion through the opening provided by the flap 70. As shown in FIG. 5, the constraining jacket 24 is orientated essentially transverse across the disc space 60. With the constraining jacket 24 properly oriented, the amorphous polymer core 22 is injected into the constraining jacket 24.

Percutaneous injection of the amorphous polymer core 22 is achieved through use of a syringe or catheter 72 which is directed to pass through the constraining jacket 24. The preferred hydrogel material of the amorphous polymer core 22, in an unhydrated state, is injected into the constraining jacket 24. A variety of methods are available for forcing the amorphous polymer core 22 into the constraining jacket 24. For example, where the amorphous polymer core 22 is comprised of a powder hydrogel material, pressurized carbon dioxide can be used to force the powder hydrogel into the constraining jacket 24. Alternatively, with hydrogel powder suspended in a liquid, or a fluid hydrogel, the amorphous polymer core 22 can be forced through the syringe 72 with manually applied pressure.

Once the amorphous polymer core 22 has been deposited, the syringe or catheter 72 is removed. In this regard, the constraining jacket 24 is preferably configured to essentially be self-sealing such that insertion and removal of the syringe or catheter 72 does not damage or otherwise impart a hole into the constraining jacket 24 large enough to allow particles of the amorphous polymer core 22 to escape. Even further, the constraining jacket 24 may be provided with a self-scaling mechanism (described above) to allow efficient introduction and removal of the syringe or catheter 72.

Figure 6:
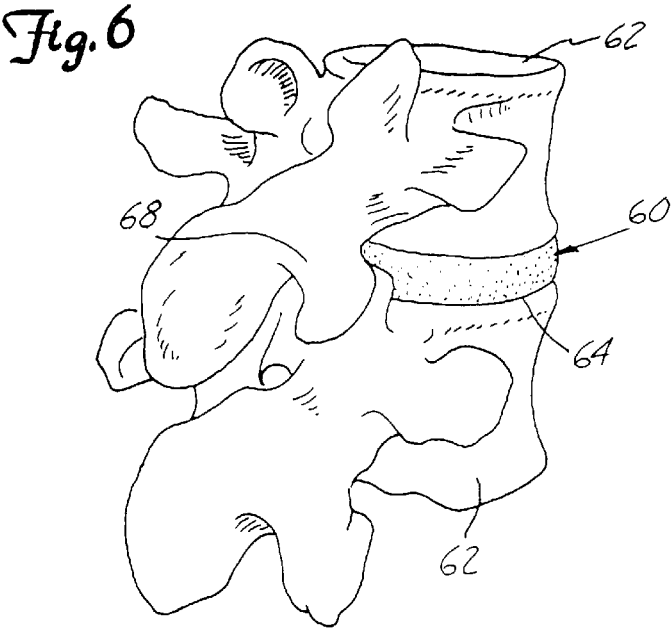
FIG. 6 is a posterior view of a spinal segment including a degenerated discal area.
Figure 7:
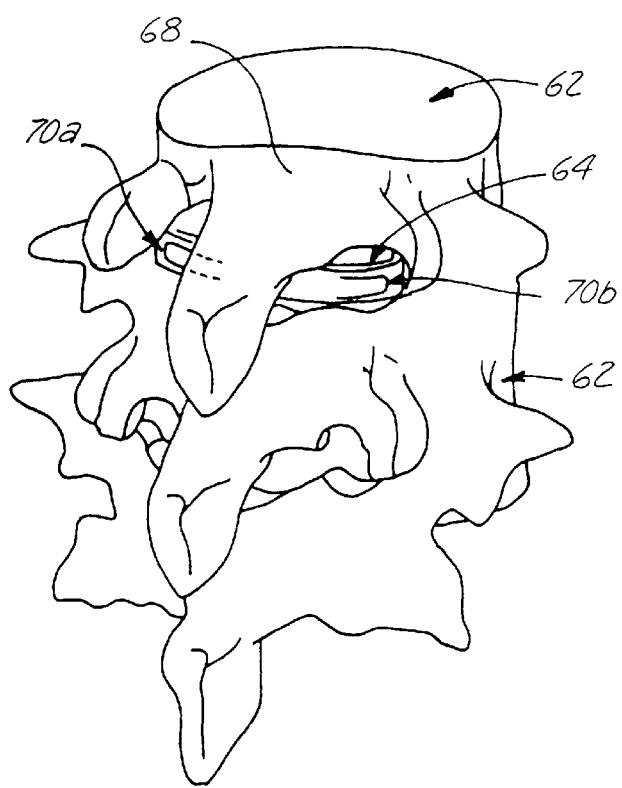
FIG. 7 is a posterior view of the spinal segment of FIG. 6 showing two flaps that have been cut through an anulus.
Figure 8:
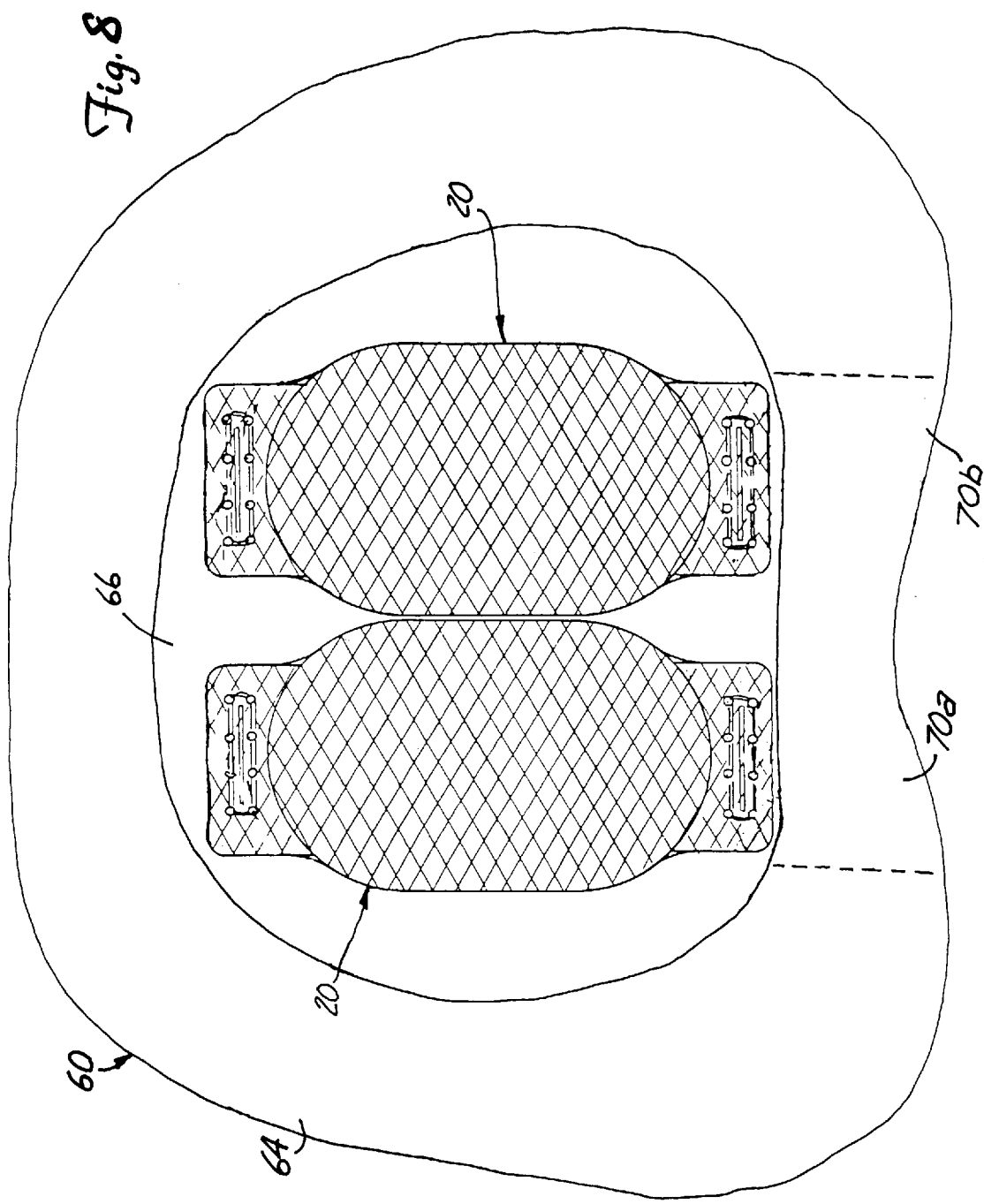
FIG. 8 is a top, sectional view of a human disc space having two prosthetic spinal disc nuclei implanted by an alternative method in accordance with the present invention.

While the preferred method has described implantation of a single spinal prosthetic disc nucleus 20 via injection of the amorphous polymer core 22, other approaches are equally acceptable. For example, the amorphous polymer core 22 and the constraining jacket 24 may be implanted as a single device. In other words, the prosthetic spinal disc nucleus 20 may be constructed (i.e., the amorphous polymer core 22 placed into the constraining jacket 24) prior to implant into the disc space 60. Even further, the prosthetic spinal disc nucleus 20 may be implanted in pairs into the damaged disc space 60 as shown in FIGS. 6–8. With this approach, a pair of flaps 70a and 70b (FIG. 7) are created in the anulus 64 to provide for passage for two of the prosthetic spinal disc nuclei 20.

The flaps 70a and 70b have a height less than a minor axis dimension of the prosthetic spinal disc nucleus 20. In a preferred embodiment, the flaps 70a and 70b have a length of about 12 millimeters and a height of about 6 millimeters for use with a prosthetic body 20 having a minor axis diameter of 7 millimeters. Importantly, because the prosthetic spinal disc nucleus 20 can be massaged to a flattened shape, the flaps 70a and 70b need not encompass the entire height of the anulus 64. Although in this example, a pair of flaps 70a and 70b are illustrated and discussed, a single flap may alternatively be used.

The vertebrae 62 adjacent the damaged disc space 60 are then slightly separated. This slight separation can be achieved by inserting an inflatable jack (not shown) through one of the flaps 70a or 70b and jacking apart the adjacent vertebrae 62. Once separation sufficient to insert a prosthetic spinal disc nuclei 20 is achieved, the flap 70a or 70b not occupied by the jack has one of the prosthetic spinal disc nucleus 20 inserted via a tapered holding tube. The jack is then deflated and removed, and a second prosthetic spinal disc nucleus 20 is placed through the remaining flap 70a or 70b.

With the alternative implantation approach, each one of the prosthetic spinal disc nuclei 20 is orientated essentially transverse across the disc space 60 as shown in FIG. 8. Once implanted, the amorphous polymer core 22 (FIG. 1) of the prosthetic spinal disc nuclei 20 begins to hydrate, imbibing surrounding fluids. To promote an increase in the rate of hydration, saline or similar fluid is injected or flushed into the nucleus cavity 66. Finally, the flaps 70a and 70b are sewn into their original position.

Regardless of the number of prosthetic spinal disc nuclei 20 implanted or whether the amorphous polymer core 22 is placed within the constraining jacket 24 before or after the constraining jacket 24 is positioned within the disc space 60, upon insertion the amorphous polymer core 22 will flow to approximately fill the constraining jacket 24 (FIGS. 5 and 8). As the hydrogel hydrates, or transitions from the unhydrated state to the hydrated state, an internal pressure is created within the constraining jacket 24. More particularly, the hydrogel-based amorphous polymer core 22 generates a swelling pressure as it expands within the constraining jacket 24. Because the constraining jacket is located between adjacent vertebrae 62, the resulting cross-sectional shape of the constraining jacket 24 is a flattened oval. With reference to FIG. 2, then, the amorphous polymer core 22 swells to fill this shape, or initial volume, of the constraining jacket 24. Notably, this initial volume is less than the generally fixed maximum volume of the constraining jacket 24 because the constraining jacket 24 is not circular in cross-section, but instead is elliptical. From this point, as the amorphous polymer core 22 continues to swell (and generate the internal pressure), the constraining jacket 24 transitions from the initial volume toward the maximum volume, increasing substantially in height ("x" in FIG. 2). The increase in height of the prosthetic spinal disc nucleus 20, in turn, forces the adjacent vertebrae 62 to lift apart and separate to a natural level.

The particulate, high surface to volume nature of the amorphous polymer core 22 allows for a faster hydration of the prosthetic spinal disc nucleus 20 than if a single, integral core body were provided, since water and body fluids will be quickly distributed throughout the amorphous polymer core 22. This rapid hydration promotes a quick expansion of the disc space 60, a rapid rise in disc height with a tightening of the circumferential, ligamentous anulus 64 and an early establishment of a barrier to dislodgment of the prosthetic spinal disc nucleus 20.

Following hydration, the preferred powdered hydrogel material of the amorphous polymer core 22 permits a small amount of slippage between individual grains and therefore a limited flow of the total core within the constraining jacket 24 as the disc space 60 is wedged during bending motions. Due to the unique design of the amorphous polymer core 22, the prosthetic spinal disc nucleus 20 is compliant, able to conform to the available internal shape of the nucleus cavity 66 defined by opposing end plates (not shown). Thus, the amorphous polymer core 22 allows for natural movements between adjacent vertebrae 62 as the viscosity of the amorphous polymer core 22 will not change as a function of shear. Even after swelling, the amorphous polymer core 22 maintains a degree of deformability, so that the prosthetic spinal disc nucleus 20 will slightly change its shape in response to physiological loads and conditions.

Following implantation, the prosthetic spinal disc nucleus 20 functions as an intervertebral spacer and a cushion, and restores the normal fluid pumping action of the disc space 60. By employing a flexible woven material for the constraining jacket 24, the amorphous polymer core 22 is allowed to deform and reform in a controlled fashion in response to physiological loads. As the amorphous polymer core 22 imbibes fluid, the constraining jacket 24 has sufficient flexibility to allow the amorphous polymer core 22 to expand. However, the strength and flexibility characteristics of the material used for the constraining jacket 24 are such that the general capsule shape of the prosthetic spinal disc nucleus 20 will always be maintained. Further, the constraining jacket 24 prevents undesirable creep of the amorphous polymer core 22 due to the substantially inelastic construction.

The prosthetic spinal disc nucleus 20 will deform and reform in response to the placement and removal of loads on the disc space 60. The prosthetic spinal disc nucleus 20 flattens in response to placement of physiologic loads on the spine, thus assuming a more flattened shape, and acts as a cushion against various loads placed upon it. As these loads are decreased (e.g., when the patient reclines), the amorphous polymer core 22 reforms, as a whole, back to a more circular cross-sectional shape. Effectively then, the constraining jacket 24 directs the amorphous polymer core 22 to reform, as a whole, vertically within the nucleus cavity 66. This controlled reformation pushes apart or further separates the adjacent vertebrae 62 (FIGS. 5 and 8), as would a normal nucleus.

The prosthetic spinal disc nucleus 20 also restores the natural fluid pumping action of the disc space 60. The hydrated prosthetic spinal disc nucleus 20 occupies a certain percentage, but not all of, the nucleus cavity 66. As loads on the disc space 60 increase, the prosthetic spinal disc nucleus 20 cushions the vertebral end plates (not shown) and slowly deforms. As a result, the volume within the nucleus cavity 60 decreases. Notably, because the prosthetic spinal disc nucleus 20 does not occupy the entire nucleus cavity 66, there is room for the prosthetic spinal disc nucleus 20 to deform, and the reduction in volume of the nucleus cavity 66 is allowed to take place as would otherwise occur with a normal nucleus. In this regard, the amorphous polymer core 22 will flatten or deform as a whole, but not decrease in volume in response to the load so that the prosthetic spinal disc nucleus 20 now occupies a larger percentage of the nucleus cavity 66. As a result of the reduction in space, fluids otherwise found in the nucleus cavity 66 are forced out of the disc space 60, thus flushing out the accumulated acids or autotoxins contained therein. Due to the preferred granule nature of the amorphous polymer core 22, more unbound or loosely bound water will flow into and out of the amorphous polymer core 22 then if a singular block material were used.

Conversely, when the load is removed or decreased, the prosthetic spinal disc nucleus 20 reforms to a more circular cross-sectional shape. This entails an increase in the vertical direction (relative to the spine in an upright position), causing the vertebral end plates (not shown) to separate, creating an increased volume in the nucleus cavity 66. It will be remembered that the amorphous polymer core 22 does not increase in volume, but simply reforms. As a result, bodily fluid, containing beneficial nutrients, fills the now-increased volume of the nucleus cavity 66, revitalizing the overall disc space 60. The prosthetic spinal disc nucleus 20 acts in concert with the natural disc space 60 to restore the natural pumping action of the disc space 60.

Notably, the prosthetic spinal disc nucleus 20 of the present invention independently absorbs the force/pressure placed upon the disc space 60. Thus, the anulus 64 is not required to support the force/pressure generated by swelling of the amorphous polymer core 22 during hydration. The anulus 64 does not provide any circumferential support to the prosthetic spinal disc nucleus 20.

E. Alternative Prosthetic Spinal Disc Nucleus Utilizing Hydrogel Material

Figure 9:
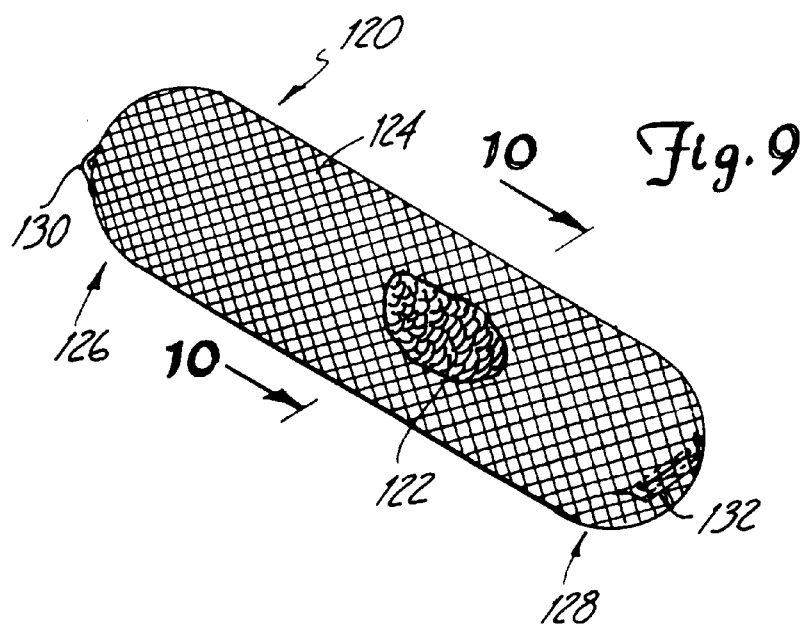
FIG. 9 is a perspective view of an alternative embodiment of a prosthetic spinal disc nucleus, including a cut-away view showing a portion of a core, in accordance with the present invention.
Figure 10:
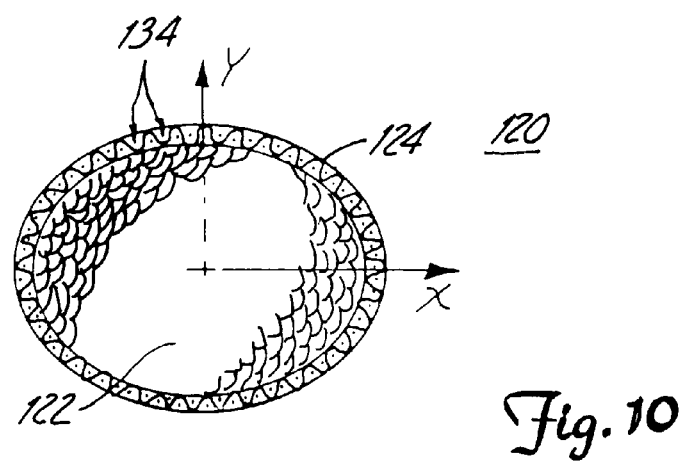
FIG. 10 is a front sectional view of the prosthetic spinal disc nucleus of FIG. 9 along the line 10—10.

An alternative embodiment of a prosthetic spinal disc nucleus 120 is shown in FIGS. 9 and 10. The prosthetic spinal disc nucleus 120 is highly similar to that previously described, in that it is comprised of an amorphous polymer core 122 and a constraining jacket 124. The constraining jacket 124 is identical to the constraining jacket 24 (FIG. 1) previously described, and includes an anterior end 126, a posterior end 128, an anterior closure 130 and a posterior closure 132. The amorphous polymer core 122, however, is defined by a plurality of hydrogel microchips. The plurality of hydrogel microchips 122 are preferably made from the same hydrogel material set forth above. Unlike the previously described amorphous polymer core 22 (FIG. 1), however, the plurality of hydrogel microchips 122 are manufactured to have a certain shape.

FIGS. 11–15 illustrate the manufacturing of the prosthetic spinal disc nucleus 120. First, a block 140 of hydrogel material is provided. The material making up the block 140 of hydrogel is preferably hydrophilic polymer, although other materials may also be useful. The block 140 of hydrogel material can be cast in any shape. In a preferred embodiment, the block 140 of hydrogel material is a cast or extruded rod of polymer approximately one millimeter in diameter. Alternatively, other dimensions may also be useful.

Figure 11:
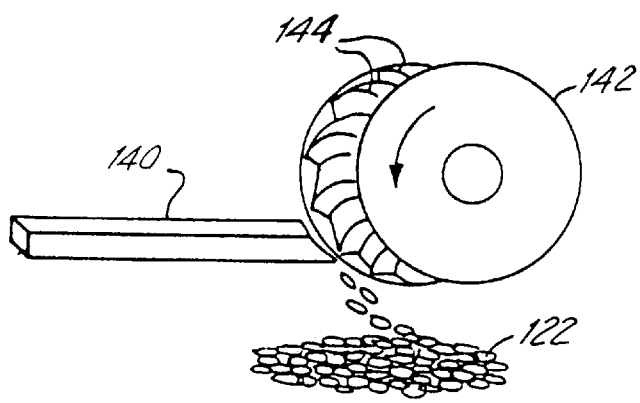
FIGS. 11–15 illustrate steps of fabricating the alternative prosthetic spinal disc nucleus of FIG. 9 in accordance with the present invention.

The block 140 of hydrogel material is fed into a holding channel (not shown) associated with a milling machine 142, as shown in FIG. 11. In a preferred embodiment, the milling machine 142 is a rotating hobbing mill 142 having a number of cutting edges 144. As the block 140 of hydrogel material is fed toward the milling machine 142, the cutting edges 144 cut the block 140 of hydrogel material, creating the plurality of hydrogel microchips 122. Because the block 140 of hydrogel is preferably amorphous and semi-rigid, the cutting edges 144 are able to easily cut the hydrogel material, resulting in a relatively uniform shape.

In a preferred embodiment, each of the plurality of hydrogel microchips 122 is approximately wedge-shaped. For example, as shown in FIG. 12A, each of the plurality of hydrogel microchips 122 is a crescent-shaped wedge, defined by a convex surface 146 and a concave surface 148. Alternatively, as shown in FIG. 12B, each of a plurality of hydrogel microchips 122'may have a more oval contour, including a slight concavity on one surface 150. Even further, as shown in FIG. 12C, each of a plurality of hydrogel microchips 122"can alternatively be an elongated body, having opposing relatively flat surfaces.

As shown by the above-described figures, the plurality of hydrogel microchips 122 can assume any of a number of wedge-shaped configurations. Preferably, however, the particular shape generated facilitates tight stacking between each of the plurality of hydrogel microchips 122. In this regard, the final shape of each of the plurality of hydrogel microchips 122 is not spherical so that at least a portion of the outer surface is not convex. With this design, the plurality of hydrogel microchips 122 can be closely compacted within the constraining jacket 124 (FIG.11), as described in greater detail below.

Figure 13:
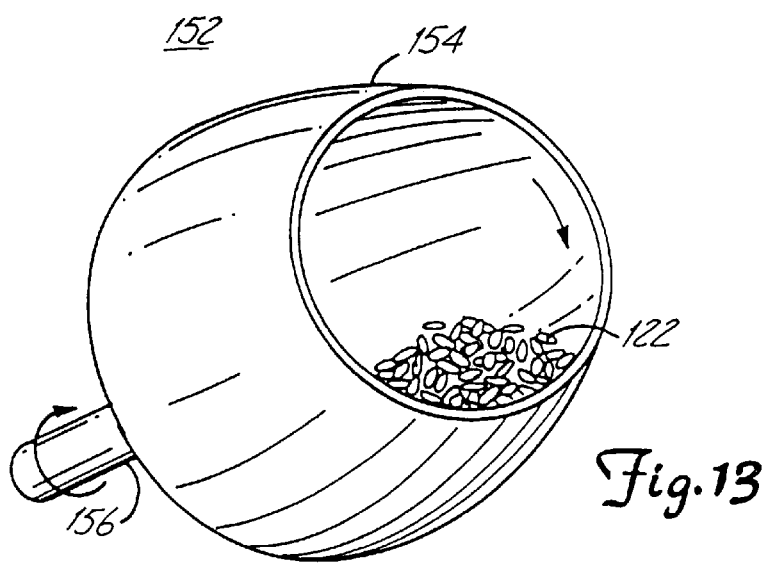
Figure 14:
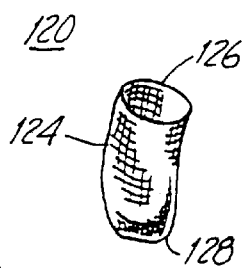
Figure 15:
Figure 12:
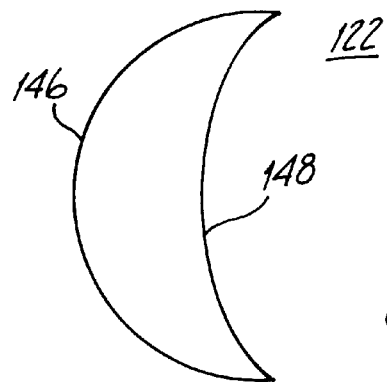
Figure 12:
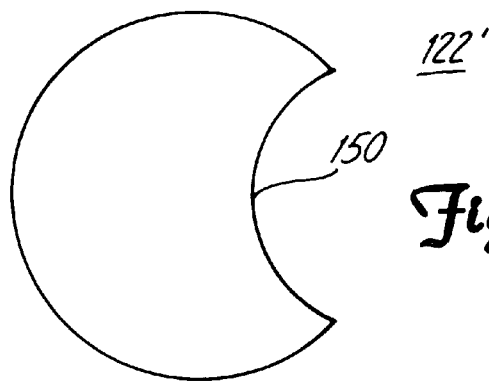
Figure 12:
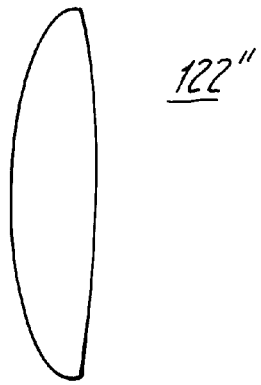

Following the cutting process, the plurality of hydrogel microchips 122 are placed into a tumbler apparatus 152, as shown in FIG. 13. In a preferred embodiment, the tumbler apparatus 152 includes a drum 154 driven by an obliquely-mounted motor shaft 156. Alternatively, other similar devices may also be used.

The plurality of hydrogel microchips 122 are first dry tumbled in the tumbler apparatus 152 so as to slightly dull their outer surface. Thus, the tumbling process abrades and polishes each of the plurality of hydrogel microchips 122, smoothing any sharp points or edges.

Any excess material removed during the dry tumbling process is separated from the drum 154, such as by a simple blowing process. Alternatively, a microfilter can be provided to filter the fine particulates from the plurality of hydrogel microchips 122 otherwise maintained in the drum 154. Following the dry tumbling process, the plurality of hydrogel microchips 122 may be slightly flattened between rotating rollers (not shown) to increase a packing density of the plurality of hydrogel microchips 122.

In the final stages of tumbling, the plurality of hydrogel microchips 122 are tumble-coated with another, softer, low friction formulation of hydrogel. The hydrogel coating may be any suitable, stable, appropriately hygroscopic material. For example, the coating may be a separate polymer having characteristics different from the material of the plurality of hydrogel microchips 122, such as a different shear behavior. Regardless of exact form, the polymer coating facilitates deformation or sliding between individual particles of the plurality of hydrogel microchips 122. As a result, a total mass formed by the plurality of hydrogel microchips 122 exhibits a deformable attribute, and is able to conform to minor variations within a nucleus cavity. In a preferred embodiment, a lower friction polyvinyl alcohol or polyacrylonitrile is used as the coating, although other similar materials may also be useful. The coating is formed as a fine, aquatic slurry that is slowly added to the drum 154 while continuously tumbling the plurality of hydrogel microchips 122. The coating material naturally adheres to the plurality of hydrogel microchips 122, forming a thin film. Following an appropriate dwell period, each of the plurality of hydrogel microchips 122 individually become thinly coated with the coating material, creating a bonded, smooth surface.

Once properly coated, the plurality of hydrogel microchips 122 are subjected to warm, filtered air and slowly dehydrated. In a preferred embodiment, forced air at a temperature of less than 100° C. is blown on the plurality of hydrogel microchips 122 while the drum 154 continues to rotate. The polishing, tumble coating and dehydration process results in coarse, free-flowing microchips, each having an approximately wedge shape.

It should be recognized that adjustments can be made in several parameters in order to achieve the desired static and dynamic behavior of the plurality of hydrogel microchips 122. For example, the viscosity and swelling behavior of the initial block 140 (FIG. 13) of hydrogel; the size and shape of each of the plurality of hydrogel microchips 122; the coefficient of friction and swelling behavior of the coating gel; and the thickness of the coating layer may be altered to achieve desired performance characteristics.

Following the tumbling process, the plurality of hydrogel microchips 122 are placed within the constraining jacket 124, as shown in FIG. 16. As previously described, the constraining jacket 124 is preferably a high molecular weight, polyethylene-woven jacket. Prior to placement of the plurality of hydrogel microchips 122, the constraining jacket 124 is closed at the posterior end 128 by the posterior closure 132. Any excess material at the posterior end 128 is removed by a thermal cut, fusing posterior closure 132.

The plurality of hydrogel microchips 122 (FIG. 13) are poured into the constraining jacket 124 at the open, anterior end 126. The anterior end 126 is then closed and any excess material is removed from the anterior end 126 by a thermal cut, fusing the anterior closure 130.

F. Alternative Prosthetic Spinal Disc Nucleus Utilizing Non-Hydrophilic Polymer

As described above, the preferred prosthetic spinal disc nucleus 20 (FIG. 1) employs a hydrogel material for the amorphous polymer core 22 (FIG. 1). It should be recognized, however, that non-hydrophilic, biocompatible polymers may also be useful. In particular, a non-hydrophilic polymer that is flowable (or can be maintained flowable) in a first state and cured or non-flowable in a second state can be used. It should be understood that the term "non-hydrophilic" as used in this specification, encompasses not only hydrophilic materials, but also materials with a slight affinity to water. Thus, any material that cannot imbibe and maintain a significant amount of water relative to an overall volume of the material is considered "non-hydrophilic". The "flowable" first state can be achieved in a number of different manners, such as by retaining the polymer in a solvent that later is released, use of a catalyst, heating the polymer to a molten state, etc. For example, silicone rubber (RTV) with acetic acid is flowable; once exposed, however, the acid is released and the silicone rubber cures.

While the non-hydrophilic polymer does not imbibe a significant amount of fluid, the resulting prosthetic spinal disc nucleus is basically identical to the preferred prosthetic spinal disc nucleus 20 shown in FIGS. 1 and 2. In other words, the substantially inelastic constraining jacket 24 is implanted into the disc space, and the amorphous polymer core 22 is percutaneously inserted into the constraining jacket 24, such as by a syringe. With the alternative embodiment, the non-hydrophilic polymer used for the amorphous polymer core 22 is inserted into the constraining jacket 24 in the first, flowable state, filling an initial volume of the constraining jacket 24 (which is less than the generally fixed maximum volume). As additional material is forced into the constraining jacket 24, a filling pressure is developed, causing the constraining jacket 24 to transition from the initial volume to the generally fixed maximum volume, increasing substantially in height ("x" in FIG. 2). In other words, the constraining jacket transitions from a flattened, oval shape to a more circular cross-section. This structural characteristic of the constraining jacket 24 is identical to the previous embodiments and results in necessary spacing between adjacent vertebrae. Once filling of the constraining jacket 24 is complete, the amorphous polymer core 22 cures, preferably remaining somewhat compliant. In the cured state, the prosthetic spinal disc nucleus 20 functions identically to the previous embodiments, acting in concert with the disc space to pump fluids into and out of the nucleus cavity.

The prosthetic spinal disc nucleus of the present invention: a) restores the height of the damaged disc space; b) restores and tightens the natural anulus to stop further degeneration and permit its healing; c) restores the normal load-unload cycling and thus flushes out toxic by-products, bringing in fresh nutrients to the disc space; d) allows a near-normal range of motion; e) relieves the movement-induced discogenic pain of the vertebral segment; and f) allows the use of a minimal, posterior surgical procedure that provides both cost and medical benefits. In short, the prosthetic spinal disc nucleus of the present invention has the ability to elevate the disc space from the inside, as does the normal, highly hygroscopic nucleus. It will tighten the ligamentous anulus and therefore promote the health and repairability of anular fibers. Beyond these functions, the prosthetic spinal disc nucleus of the present invention has the unique ability to conform to contours of the available internal nucleus cavity. Further, the prosthetic spinal disc nucleus will exhibit shear behavior under load, imitating the normal, constrained rheology of the natural disc nucleus. Finally, hospital inventory costs are greatly reduced in that the final size of the prosthetic spinal disc nucleus need not be determined until actual surgery. The surgeon then simply chooses an appropriately sized constraining jacket and subsequently inserts a sufficient amount of the amorphous polymer core.

Although the present invention has been described with reference to preferred embodiments, workers skilled in the art will recognize that changes may be made in form and detail without departing from the spirit and scope of the invention. For example, other methods of sealing the ends of the constraining jacket exist, such as heat, ultrasound, crimp ring seals or spin entanglement. Additionally, more than a single layer of material may be used to maintain the integrity of the amorphous polymer core. In other words, a plurality of jackets can surround the amorphous polymer core with one layer providing efficient filtering of the amorphous polymer core and assure full containment, and a second layer providing strength.

What is claimed is:

1. A prosthetic spinal disc nucleus for implantation into a nucleus cavity of a spinal disc, the nucleus cavity defined by an opposing pair of vertebral bodies, forming opposing end plates, and an anulus, the prosthetic spinal disc nucleus comprising:

a substantially inelastic constraining jacket having a generally fixed maximum volume determined by a generally fixed circumference and length, the maximum volume being less than a volume of the nucleus cavity, wherein the constraining jacket defines a height corresponding to a plane substantially perpendicular to the opposing end plates, and further wherein, upon implantation, the constraining jacket is configured such that the opposing end plates force the constraining jacket to an initial implant volume in which the constraining jacket is oval in cross-section; and an amorphous polymer core inserted into the constraining jacket, the polymer core configured to be flowable in at least a first state such that upon insertion, the amorphous polymer core fills the initial implant volume of the constraining jacket and creates an internal pressure within the constraining jacket, the constraining jacket being configured to transition from the initial implant volume toward the maximum volume, increasing substantially in height in response to the internal pressure.

2. The prosthetic spinal disc nucleus of claim 1, wherein the amorphous polymer core is configured to conform to a contour of the disc space.

3. The prosthetic spinal disc nucleus of claim 1, wherein the amorphous polymer core is a non-hydrophilic polymer, and wherein the internal pressure is a filling pressure of the amorphous polymer core upon insertion into the constraining jacket.

4. The prosthetic spinal disc nucleus of claim 1, wherein the amorphous polymer core is a hydrogel configured to expand from an unhydrated state to a hydrated state.

5. The prosthetic spinal disc nucleus of claim 4, wherein the maximum volume of the constraining jacket is greater than a volume of the amorphous polymer core in the unhydrated state, but less than a volume of the amorphous polymer core in the hydrated state, and wherein the internal pressure is a swelling pressure of the amorphous polymer core transitioning from the unhydrated state to the hydrated state.

6. The prosthetic spinal disc nucleus of claim 4, wherein the hydrogel is a hydrogel powder.

7. The prosthetic spinal disc nucleus of claim 6, wherein the hydrogel powder consists of a plurality of irregularly shaped granules.

8. The prosthetic spinal disc nucleus of claim 7, wherein each of the plurality of irregularly shaped granules is flattened, having a height less than a width or a length.

9. The prosthetic spinal disc nucleus of claim 7, wherein the plurality of irregularly shaped granules is coated with a low friction material.

10. The prosthetic spinal disc nucleus of claim 6 wherein the hydrogel powder includes a plurality of non-spherical granules.

11. The prosthetic spinal disc nucleus of claim 6, wherein the hydrogel powder is suspended in a viscous liquid.

12. The prosthetic spinal disc nucleus of claim 4, wherein the hydrogel is a fluid hydrogel.

13. The prosthetic spinal disc nucleus of claim 12, wherein the fluid hydrogel is configured to congeal upon contact with water.

14. The prosthetic spinal disc nucleus of claim 13, wherein the fluid hydrogel is non-thixotropic.

15. The prosthetic spinal disc nucleus of claim 1, wherein the amorphous polymer core comprises a plurality of hydrogel microchips.

16. The prosthetic spinal disc nucleus of claim 15, wherein at least a portion of an outer surface of each of the plurality of hydrogel microchips is flattened.

17. A method of manufacturing a prosthetic spinal disc nucleus implanted into a nucleus cavity of a spinal disc, the method comprising:

providing a substantially inelastic constraining jacket having a generally fixed maximum volume determined by a generally fixed circumference and length, the maximum volume being less than a volume of the nucleus cavity, and wherein the constraining jacket defines a height corresponding to a transverse plane of the nucleus cavity, and further wherein the constraining jacket is configured such that upon implantation, the constraining jacket is forceable to an initial implant volume in which the constraining jacket is oval in cross-section;

providing an amorphous polymer core that is flowable in at least a first state;

inserting the amorphous polymer core in the first state into the constraining jacket such that the amorphous polymer core fills the initial implant volume of the constraining jacket; and generating an internal pressure within the constraining jacket, wherein the constraining jacket transitions from the initial implant volume toward the maximum volume, increasing substantially in height in response to the internal pressure.

18. The method of claim 17, wherein providing an amorphous polymer core includes forming a hydrogel configured to expand from an unhydrated state to a hydrated state.

19. The method of claim 18, wherein the amorphous polymer core is inserted into the constraining jacket in the unhydrated state, and wherein generating an internal pressure includes hydrating the amorphous polymer core to the hydrated state.

20. The method of claim 17, wherein the amorphous polymer core is a non-hydrophilic polymer and wherein generating an internal pressure includes injecting a volume of the non-hydrophilic polymer into the constraining jacket greater than the initial implant volume of the constraining jacket to develop a filling pressure.

21. The method of claim 17, wherein providing an amorphous polymer core includes providing a hydrogel powder.

22. The method of claim 21, wherein providing an amorphous polymer core further includes:

coating individual grains of the hydrogel powder with a low friction material.

23. The method of claim 17, wherein providing an amorphous polymer core includes suspending a hydrogel powder in a viscous liquid.

24. The method of claim 17, wherein providing an amorphous polymer core includes providing a fluid hydrogel.

25. The method of claim 24, wherein providing a fluid hydrogel includes dissolving a hydrogel powder in a solvent such that the fluid hydrogel will congeal upon hydration.

26. The method of claim 17, wherein providing an amorphous polymer core includes forming a plurality of hydrogel microchips.

* * * * *